United States Patent [19]

Friesen et al.

[11] 4,438,771
[45] Mar. 27, 1984

[54] PASSIVE CONTACTLESS MONITOR FOR DETECTING CESSATION OF CARDIOPULMONARY

[75] Inventors: W. Otto Friesen; Gene D. Block, both of Charlottesville, Va.

[73] Assignee: University of Virginia Alumni Patents Foundation, Charlottesville, Va.

[21] Appl. No.: 371,933

[22] Filed: Apr. 26, 1982

[51] Int. Cl.³ .......................... A61B 5/08; A61B 5/10
[52] U.S. Cl. .................................. 128/671; 128/721; 340/573
[58] Field of Search .................. 128/716, 721–723, 128/670, 671; 340/573; 128/782, 774

[56] References Cited

U.S. PATENT DOCUMENTS

| | | | |
|---|---|---|---|
| 3,991,746 | 11/1976 | Hanna | 128/722 |
| 4,033,332 | 7/1977 | Hardman | 128/722 |
| 4,320,766 | 3/1982 | Alihanka et al. | 128/722 X |

Primary Examiner—Kyle L. Howell
Assistant Examiner—John C. Hanley
Attorney, Agent, or Firm—Oblon, Fisher, Spivak, McClelland & Maier

[57] ABSTRACT

An apparatus and method is disclosed for detecting the cessation of movement of a body by detecting the voltage produced by the movement of the charge on said body because of the body's movement. This is accomplished by a passive contactless conductive pad which is spaced from the body and in which a potential is induced by the movement of the body through the movement of the charge on the body. This potential is amplified and an alarm indication device responds to the amplified potential to produce an alarm when the output of the amplifier is below a predetermined value or for a predetermined period of time. This device enables the unattended monitoring of breathing and heart functioning for long periods of time.

10 Claims, 6 Drawing Figures

PASSIVE CONTACTLESS MONITOR FOR DETECTING CESSATION OF CARDIOPULMONARY

BACKGROUND OF THE INVENTION

1. Field of the Invention

This invention relates to a contactless system for monitoring the condition of the body or either a human or an animal and providing an alarm upon detection of a cessation of activity for a predetermined time.

2. Description of the Prior Art

The field of respiration and heart monitoring has generally been addressed in the prior art to types of devices which are used in hospitals and which have a level of sophistication requiring complex circuitry and a sizable expense. These monitoring devices have usually taken the form of respiration monitors which are used mainly in hospitals to signal a nurse when a human patient has stopped breathing. Among the most prominent of these devices is the monitoring device which utilizes the connection of electrodes directly to the skin of a patient in order to sense electrical resistance changes during respiration in the skin surrounding the expanding and contracting chest cavity. Quite obviously the connection of electrodes directly to the patient is not only a problem with regard to providing satisfactory contact due to irritation and skin rashes which result from a saline solution commonly used to provide satisfactory contact but also, this method provides several problems with regard to maintaining the contact as the patient moves.

One of the more pertinent problems in recent years has been the detection of apnea which occurs in infants and is primarily a cessation of voluntary breathing. This problem has come to be known as "the sudden infant death syndrome" (SIDS). As is now known in the medical field, the monitoring and surveillance of infants and especially infants who have been determined to be high risk during the critical first six months is seen to save many lives and at least provide information concerning the cause of this syndrome.

Quite obviously, the continuous monitoring of an infant for its first six months of its life is a process which cannot take place in a hospital because most of the problems with the detection and the determination of this syndrome is the fact that there are no warning signs which are given prior to its occurrence. Therefore, home monitoring is the most useful and most assuring method of saving lives. The basis of operation for the detection of the syndrome is the cessation of breathing which can be corrected by cutaneous stimulation. In other words, once breathing has stopped and all heart functions have stopped for a period of anywhere from 10 seconds to a minute, the infant's life may still be saved if the proper technique is used. However, most prior art devices require an extreme expense on the part of the parents to either rent or purchase the complicated devices for the home monitoring. Furthermore, these devices have problems with regard to false alarms primarily because of proper placement and retention of the sensor on the child who turns or moves in his sleep.

More recent attempts to solve these problems involve the use of pressure monitoring devices which rely on a monitoring of the activity of a child by changes in a pressure transducer located beneath the child, which changes are induced by the breathing of the child. These transducer devices such as shown in U.S. Pat. No. 4,033,332 require an active electrical bias for the pad upon which the infant is resting. In other words, these devices produce a change in the electrical capacitance in the pad when the child moves, which change is pressure related, and which change causes a signal to be developed which can be monitored. When the changes in the pressure have ceased for a period of time no change in capacitance is detected and an alarm is registered.

As indicated, these types of pressure monitoring devices require both an electrical circuit for the pad and for the monitoring of the output signal from the pad. Thus, not only must the cost of the device be extremely high but is must also be properly adjusted for the weight of the child, which changes the capacitance detected, and for the proper electrical functioning of the two separate circuits for the pad and for the signal developed from the pad.

Aside from the obvious requirement in the prior art of a separate power supply for the pad structure which requires a 110 volt source, there is the associated psychological and convenience barrier in the mind of the parents who may be apprehensive about placing something underneath their child or very close to their child which is plugged into an electrical outlet for long periods of time. Another inherent disadvantage is that these type of monitoring systems may not be used in bassinetts or portable carriers because of their size and the obvious requirement of a 110 volt source.

Lastly, the criticality of the weight factor with regard to the adjustment of the device would require adjustment of the sensing device as the weight of the child increases with age, and of course would be sensitive to other weighted objects in the crib such as toys, stuffed animals etc.

It is the object of the present invention to provide a passive contactless monitoring device which overcomes the disadvantages of the prior art.

SUMMARY OF THE INVENTION

Accordingly, one object of this invention is to provide a novel monitoring system which is passive in nature, requires no contact with the body of the person or animal being monitored and which does not use or require a 110 volt source. This is accomplished according to the present invention by taking advantage of the movement of the charge which takes place upon the movement of any human or animal body which movement of charge induces a potential in a conductive material.

The device according to the present invention provides for an apparatus which detects the cessation of movement of a body in which the body does not contact the apparatus and in which the apparatus has a passive charge variation conductive pad spaced from the body which is being monitored and in which a potential is induced by any movement of the body either from the respiratory function or the cardiac function. This induced potential is amplified in order to produce a voltage output which is representative of movement of the body and in order to give a signal to an alarm indicator which is responsive to the voltage in order to produce an indication signal when the output of the amplifying device is below a predetermined value for a predetermined period of time.

Another object of the present invention is to provide a thin construction of the conductive apparatus including alternating layers of plastic and conductive material which can cover the entire area underneath or near the body to be monitored regardless of the weight of the body to be monitored.

A further object of the present invention is to provide a reliable, inexpensive apparatus which can be used in the home environment and can be battery operated without the necessity of an attachment to an electrical outlet and without the necessity of modifying the environment of the person or infant being monitored with regard to other objects in the crib or the changing position of an infant during long periods of unattended monitoring.

A still further object of the invention is to provide a device sensitive enough to detect motion induced by either the respiratory function or the cardiac function to provide a double measure of security and assurance to the parents during long periods of unattended monitoring.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

DESCRIPTION OF THE PREFERRED EMBODIMENTS

Figure 1:
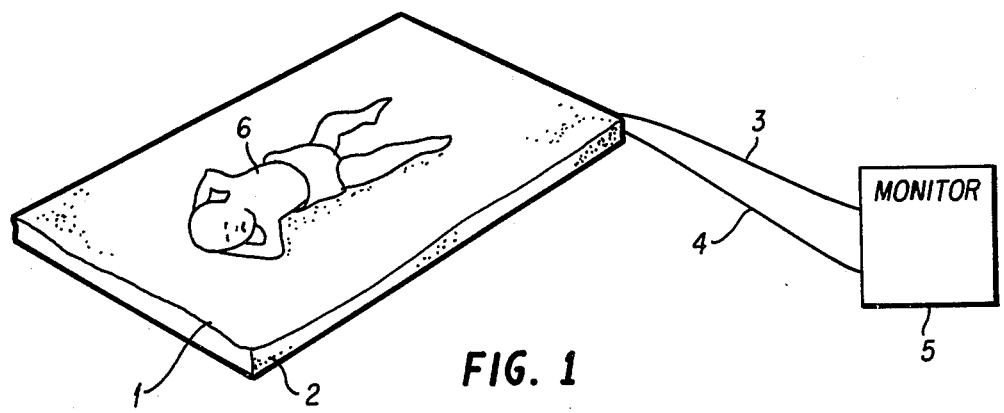
FIG. 1 is a perspective view of the conductive pad arrangement on a mattress or bed upon which a infant is shown.

Referring now to the drawings, wherein like references numerals designate identical or corresponding parts throughout the several views, and more particularly to FIG. 1 thereof, there is shown a perspective view of the conductive pad arrangement 1 which is placed on top of a mattress or bed 2. The leads 3 and 4 connect the conductive pad 1 to the monitoring section 5 which provides the alarm function as will be described below. Shown upon the pad 1 is an infant 6 who may be placed at any position on the pad and who may be of any size, including an adult or animal, regardless of its weight.

Figure 2:
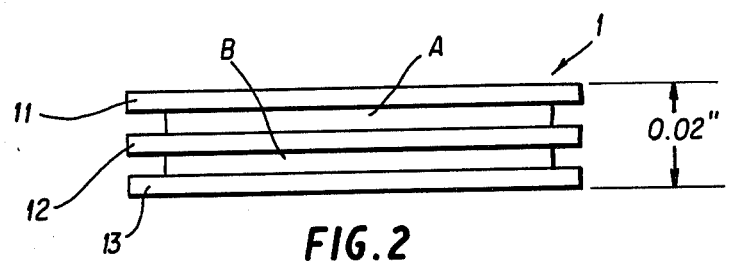
FIG. 2 is a side view of the conductive pad of FIG. 1.

FIG. 2 shows a side view of the conductive pad arrangement 1 which contains conductive layers A and B enclosed by plastic sheet layers 11, 12 and 13. The length of the conductive pad layers is shown to be slightly smaller than the length of the plastic layers for purposes of providing an area where sealing may be accomplished between the plastic layers to affectively encapsulate the conductive pads A and B with a plastic layer 12 located therebetween.

Each human body or animal body contains a net or at least a accumulation of charge. Thus the infant represented as 6 in FIG. 1 contains a certain amount of charge. When there is movement of a charge, a potential is induced in a conductive material such as the conductive pad 1 or 20. Thus the movement of the infant 6 either through its breathing or its heart beat causes a potential in each of the layers A and B. Effectively then, the electrode lines 3 and 4 each carry a voltage from the layers B and A respectively which is fed to a monitor circuit 5. This monitor circuit 5 consists of an amplification portion shown in FIG. 5 and a alarm indicator portion shown in FIG. 6. The effect of this monitor device is to amplify the voltage induced onto the potential electrodes 3 and 4 to provide an indication of movement of the infant 6. The amplifier and the alarm indicator circuit as constructed and discussed below, is set up in such a manner that an alarm is indicated when a potential is not induced on the lines 3 and 4 for a predetermined period of time.

That is, the alarm functions when the body 6 has not either had a heart beat or a resipatory function within a predetermined period of time. This provides an alarm indication to, for example the parents, to start the artificial respiratory procedures necessary to induce the continued rhythmatic breathing.

Figure 3:
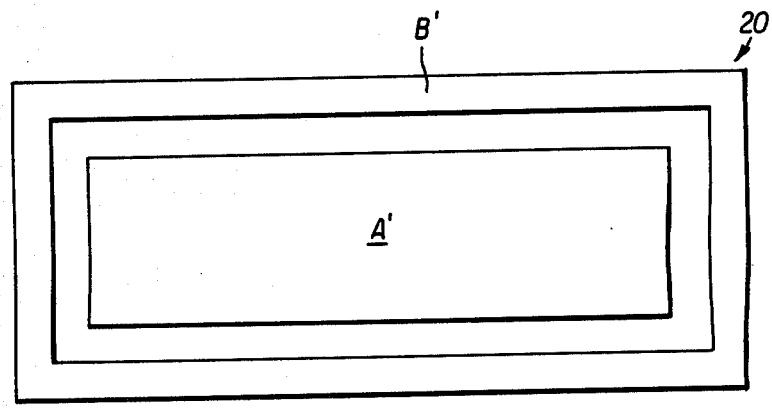
FIG. 3 is a top view of an alternate embodiment of the conductive pad of the present invention.
Figure 4:
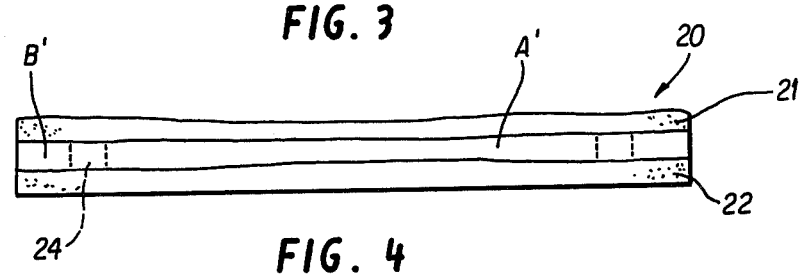
FIG. 4 is a side view of the alternate embodiment of the conductive pad arrangement.

An alternate embodiment for the construction of the pad and the pad layers is shown in FIGS. 3 and 4 wherein the pad 20 has a side by side construction for the layers A' and B' with an air space located between. The central rectangular pad A' is surrounded by a central rectangular spacing labeled 24 which in turn is surrounded by the conductive layer B'. Each of the layers A' and B' and the space 24 is enclosed by top and bottom plastic layers 21 and 22 respectively. The lead connections 3 and 4 shown in FIG. 1 is equally applied to the structure of FIGS. 3 and 4 with each of the leads 3 and 4 being respectively connected to the layers B' and A'.

Figure 5:
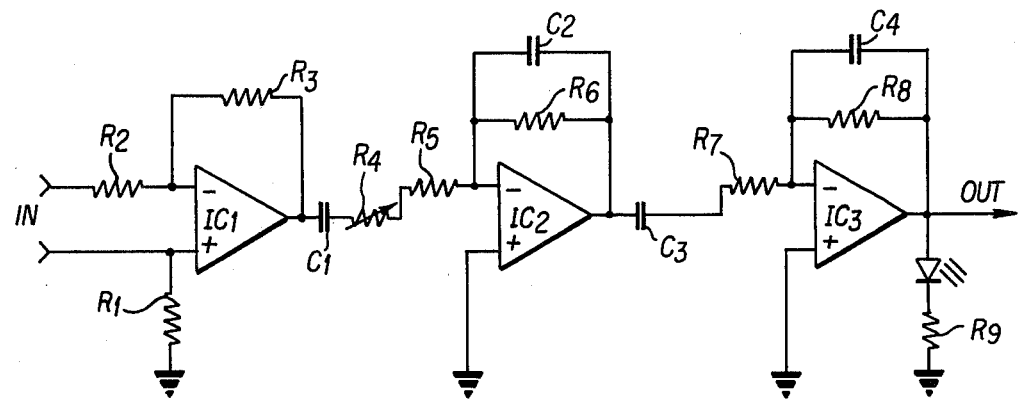
FIG. 5 is a schematic drawing of an exemplary amplifier section of the present invention.
Figure 6:
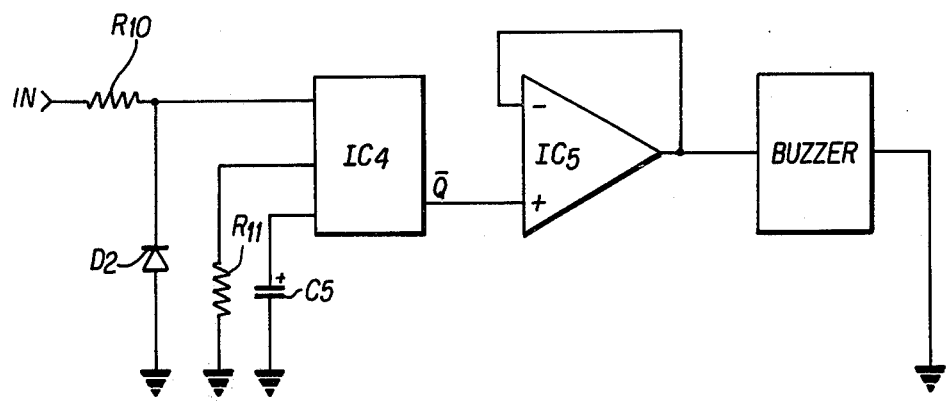
FIG. 6 is an exemplary schematic diagram of the alarm indicator section of the present invention.

The amplifier portion shown in FIG. 5 consists of three stages of amplification including the respective three operational amplifiers IC1, IC2 and IC3. The conductors A and B or A' and B' are connected to the input of the first amplification stage through resistors R2 and R1 respectively. Each of the operational amplifiers are constructed of a CMOS operational amplifier with a very high input impedance. The normal feedback operation for the amplifier section is shown by the resistance R3. The purpose of resistor R1 is to slowly discharge the plate attached thereto so that only movements of charged objects but not stationary objects are detected. Because all physical bodies bear a net charge, movement near the sensor plate will induce potential changes on both plates so that the first amplification stage actually amplifies the difference between the potentials of the two plates. The difference in resistance between R1 and R2 provides a difference between the two voltages which is then amplified. The potentiometer R4 allows the overall amplification to be varied by a factor of 10. The capacitors C1–C4 are components of a band pass filter which eliminates undesirable low frequency and high frequency noises. By choosing appropriate values for the capacitors C1–C4 of the band pass filters, either heart beat, breathing movements or both heart beat and breathing movements can be detected. This apparatus is sensitive enough to detect the breathing movements of small infants, even when the sensor plate is placed below the mattress pad. The device has been tested to function successfully with infants weighing as little as 6 pounds.

The output of the amplifier section and most particularly, the amplifier IC3 is connected to the input of an edge-triggered retriggerable one-shot, IC4. The pulse duration of the one-shot is set with R10 and C5 to 20 seconds. Thus if any large amplitude voltage swing occurs at the amplifier output at intervals of less than 20 seconds the $\overline{Q}$ output of the one-shot will remain low. If no such fluctuations occur for more than 20 seconds, the $\overline{Q}$ will go high and, via buffer IC5, drive the buzzer as shown. The 20 seconds is adjustable by means of the above-mentioned R10 and C5.

Other monitoring features are possible with the present invention such as a light which would indicate by a flashing with each output of the amplifier to indicate either a breathing or a heart action. This can occur through the use of the diode D1 and the resistor R9 shown in FIG. 5 at the output of the amplifier circuitry.

The remaining circuitry, including the diode D2 and the resistors R11, provide the necessary connections for the one-shot operation. Likewise, any other amplifier device which can amplify the potential on the electrodes 3 and 4 of FIG. 1 may be used in order to drive the alarm indicator means and certainly other alarm circuitry, known to those skilled in the art, may be used to provide the necessary indications of cessation of breathing or cardiac movement.

The conductive layer used in the above embodiment employed aluminum foil, however, other workable conductive layers can be constructed of copper wire mesh, conductive plastic and the like.

The following lists of resistor and capacitor values indicate the example shown and described above with respect to FIGS. 5 and 6 and are not meant to be limiting. Resistors R1, 20M; R2, 1M; R3, 20M; R4, 100K (pot); R5, 10K; R6, 1; R7, 10K; R8, 1M; R9, 1K; R10, 100K; R11, 330K; Cl, 100 μF; C2, 0.1 μF; C3, 100 μF; C4, 0.1 μF; C5, 100 μF.

The amplifier sections consisting of operational amplifiers IC1, IC2 and IC3 consists of ½ of a 353 CMOS chip, with the diode D1 being a light emitting diode (LED) and the diode D2 being a IN4148.

The above describe monitoring device presents a passive contactless system which can be easily constructed and inexpensively made to enable, for example, parents to purchase these devices for home use during the first several critical months of an infant's life, either as a routine cautionary procedure or as instructed by a physician in the instances where the SIDS is most likely to occur. This is particularly important with infants who have had previous occurrences of this syndrome or for parents have had other children who have died in this manner.

The reliability and moderate costs of this device provides a significant area of improvement in the monitoring, at home, of infants through the first several critical months of their life.

The passive pad i.e., requiring no active electrical source, permits the entire circuits to be battery operated without a need for a 110 volt source and without the need to place a baby on a pad which is attached to a voltage source for long periods of time.

Obviously, numerous modifications and variations of the present invention are possible in light of the above teachings, particularly with regard to the construction of the amplifier and alarm circuitry. It is therefore to be understood that within the scope of the appended claims, the invention may be practiced otherwise than as specifically described herein.

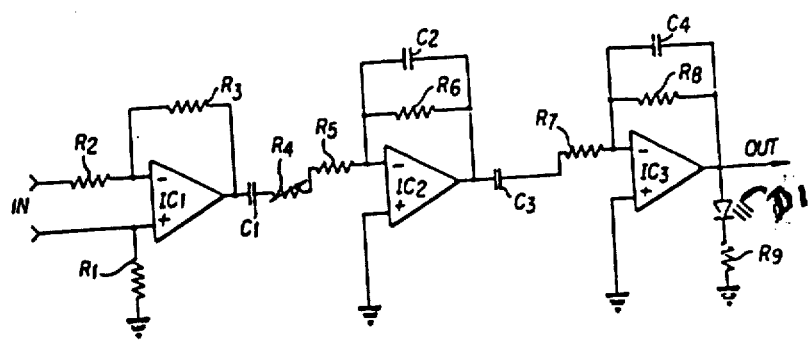

What is claimed as new and desired to be secured by Letters Patent of the United States is:

1. An apparatus for detecting cessation of cardiopulmonary functioning of a human body, comprising:
   a passive conductive means, spaced apart from said body in which a potential is directly induced by the movement of said body due to the movement of the charge of said body when said cardiopulmonary functioning occured;
   monitor means responsive to said directly induced potential to produce a indication of cessation of cardiopulmonary functions of said body.

2. The apparatus according to claim 1 wherein said monitor means includes a potential amplification means response to said induced potential to produce a voltage output representative of movement of said body and an alarm indication means responsive to the output of said amplifier means to produce an indication signal by the output of said amplifier means is below a predetermined value for a predetermined period of time.

3. An apparatus for detecting cessation of movement of a body containing a charge comprising:
   a passive charge movement detecting conductive means spaced from said body in which a potential is directly induced on said conductive means by the movement of said charge caused by the movement of said body;
   potential amplification means responsive to said induced potential to produce a voltage output representative of movement of said body; and
   alarm indicator means responsive to the output of said amplification means to produce a signal indicating the cessation of movement of said body when the output of said amplification means is below a predetermined value for a predetermined period of time.

4. The apparatus of claim 1 wherein said passive charge movement detecting conductive means consists of a pair of conductive layers separated by an insulating layer and wherein said conductive means is spaced from said body by at least a covering plastic layer.

5. The apparatus according to claim 1 wherein said passive charge variation detecting conductive means comprises;
   a first conductor; and
   a second conductor spaced apart from said first conductor concentric with said first conductor and with said second conductor located entirely in the same horizontal plane as said first conductor.

6. The apparatus according to claim 1 wherein said potential amplification means responsive to said induced potential has a variable amplification factor in order to adjust the sensitivity of said conductive means.

7. An apparatus according to claim 1 wherein said potential amplification means includes an output display response to said voltage output to produce a visual indication of body movement.

8. An apparatus according to claim 3 wherein said potential amplification means and said alarm indication means are constructed in a same unit and said unit is attached to said conductive means by leads.

9. A method for detecting cessation of movement of a body containing a charge, comprising the steps of:
   detecting the movement of said body by means of a measurement of a potential directly produced as a result of said movement of said charge caused by the movement of said body;
   outputting by means of a passive conducting means, said potential produced by said movement;

amplifying said outputted potential to produce a voltage output representative of body movement; and producing an alarm indicating cessation of movement of said body when said voltage output is below a predetermined value for a predetermined period of time.

10. The method of claim 9 including the further steps of encapsulating said conductive means in plastic and placing said encapsulated conductive means beneath said body to be monitored.

* * * * *

UNITED STATES PATENT AND TRADEMARK OFFICE
CERTIFICATE OF CORRECTION

PATENT NO.   : 4,438,771
DATED        : MARCH 27, 1984
INVENTOR(S)  : W. OTTO FRIESEN ET AL

It is certified that error appears in the above-identified patent and that said Letters Patent is hereby corrected as shown below:

Item 54 (Title): insert the word --ACTIVITY-- after "CARDIO-PULMONARY".

Figure 5 should read as shown on the attached sheet.

Column 1: insert the word --ACTIVITY-- after "CARDIOPULMONARY".
  line 9, change the word "or" to --of--.

Column 3: line 61, change the word "affectively" to --effectively--.

Column 5: line 1, change "R10" to --R11--;
  line 8, change "R10" to --R11--;
  line 16, change "R11" to --R10--;
  line 40, change "describe" to --described--.

Column 6: line 13, change "response" to --responsive--.

Signed and Sealed this

Twenty-third Day of October 1984

[SEAL]

Attest:

GERALD J. MOSSINGHOFF

*Attesting Officer*   *Commissioner of Patents and Trademarks*